United States Patent [19]

Ross et al.

[11] 4,166,818

[45] Sep. 4, 1979

[54] ACYLAMINO DERIVATIVES

[75] Inventors: William J. Ross, Lightwater; John P. Verge, Henley-on-Thames; William R. N. Williamson, Slough, all of England

[73] Assignee: Lilly Industries Limited, London, England

[21] Appl. No.: 840,885

[22] Filed: Oct. 11, 1977

Related U.S. Application Data

[63] Continuation of Ser. No. 691,952, Jun. 1, 1976, abandoned.

[30] Foreign Application Priority Data

Jun. 5, 1975 [GB] United Kingdom ............... 24224/75

[51] Int. Cl.$^2$ .................. C07D 271/06; C07D 285/08
[52] U.S. Cl. ............................. 548/128; 260/239.3 R; 548/133; 548/130; 548/132; 424/270; 424/272; 542/414; 542/421; 546/209
[58] Field of Search .................. 260/307 G, 306.8 D, 260/239.3, 293.68, 293.67; 542/414, 421

[56] References Cited

U.S. PATENT DOCUMENTS

| | | | |
|---|---|---|---|
| 3,629,275 | 12/1971 | Metzger et al. | 260/306.8 D |
| 3,720,684 | 3/1973 | Krenzer et al. | 260/306.8 D |

FOREIGN PATENT DOCUMENTS

| | | | |
|---|---|---|---|
| 1235761 | 6/1971 | United Kingdom | 260/306.8 D |
| 1396941 | 6/1975 | United Kingdom | 260/307 |

OTHER PUBLICATIONS

Selim et al., Bull. Soc. Chim., France, 1967, pp. 1219–1220.
Neville et al., Derwent Abstract, No. 43048w/26.
Selim et al., Chemical Abstracts, vol. 67, abstract No. 54082e (1967).

*Primary Examiner*—Alton D. Rollins
*Attorney, Agent, or Firm*—Nancy J. Harrison; Everet F. Smith

[57] ABSTRACT

Acylamino heteroaryl compounds in which the heteroaryl nucleus is a 1,2,4-oxadiazole or 1,2,4-thiadiazole nucleus, methods of making the compounds and pharmaceutical formulations containing the compounds. The compounds have anti-allergy activity.

21 Claims, No Drawings

ACYLAMINO DERIVATIVES

This is a continuation, of application Ser. No. 691,952, filed June 1, 1976, now abandoned.

This invention relates to heterocyclic chemical compounds, more particularly to certain novel 5-membered heteroaryl derivatives substituted by an acylamino group which are useful for the chemotherapy of immediate hypersensitivity conditions and/or which are useful as intermediates in the preparation of such active compounds. The invention also includes processes for preparing the active compounds of the invention. Furthermore, the invention includes within its scope pharmaceutical compositions containing pharmacologically active compounds and methods of treatment of animals, including humans, comprising administering thereto an effective dose of the compound or compounds or of pharmaceutical compositions comprising the active compound or compounds of the invention.

Compounds similar to those of the present invention have been previously described in *Bull. Soc. Chim.*, 1219, (1967); however, it is to be noted that this article discloses no utility whatsoever and is of academic interest only.

It is an object of the present invention to provide compounds useful in the chemotherapy of immediate hypersensitivity conditions.

Accordingly, the present invention provides a novel heteroaryl derivative of the formula:

$$Ar-N-R^1 \quad (I)$$
$$\phantom{Ar-N-}COR^2$$

wherein Ar represents a 1,2,4-oxadiazole or 1,2,4-thiadiazole nucleus optionally substituted by formyl, carboxyl, hydroxyl, $C_{1-4}$ hydroxyalkyl, $C_{1-4}$ alkyl, $C_{3-10}$ cycloalkyl, $C_{3-6}$ acyloxyalkyl, optionally substituted phenyl or halogen, the acylamino group $-NR^1COR^2$ being attached to a carbon atom of the heteroaryl ring, and wherein $R^1$ is $C_{1-10}$ alkyl, $C_{2-6}$ alkenyl, $C_{2-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, optionally substituted phenyl-$C_{1-6}$ alkyl or optionally substituted phenyl-$C_{2-6}$ alkenyl; and $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, optionally substituted phenyl, optionally substituted phenyl-$C_{1-6}$ alkyl or optionally substituted phenyl-$C_{2-6}$ alkenyl; or $R^1$ and $R^2$ together form a lactam ring having 5 to 7 ring atoms; provided that:
when Ar is 1,2,4-oxadiazolyl substituted by phenyl, $R^1$ cannot be methyl or benzyl when $R^2$ is methyl.

The optional substituent on the on the heteroaryl nucleus is preferably selected from $C_{1-4}$ alkyl, $C_{3-8}$ cycloalkyl and phenyl. Preferred $R^1$ substituents are $C_{1-8}$ alkyl, $C_{3-6}$ alkenyl, $C_{3-8}$ cycloalkyl and benzyl optionally substituted by halogen, $C_{1-4}$ alkyl or $C_{1-4}$ alkoxy. Preferred $R^2$ substituents are $C_{1-8}$ alkyl, $C_{3-8}$ cycloalkyl, benzyl and phenyl optionally substituted by halogen or $C_{1-4}$ alkoxy.

The term "$C_{1-6}$ alkyl" as used herein means a straight or branched chain alkyl group containing from 1 to 6 carbon atoms such as methyl, ethyl, iso-propyl, n-butyl, s-butyl, isobutyl, t-butyl, n-amyl, s-amyl, n-hexyl, 2-ethylbutyl or 4-methylamyl.

Similarly the term "$C_{1-4}$ alkyl" as used herein means a straight or branched chain alkyl group containing from 1 to 4 carbon atoms, namely methyl, ethyl, isopropyl, n-propyl, n-butyl, isobutyl, s-butyl, t-butyl. "$C_{1-4}$ hydroxyalkyl" and "$C_{3-6}$ acyloxyalkyl" means the aforementioned $C_{1-4}$ alkyl groups substituted with an hydroxy group and acyloxy group respectively. "$C_{2-6}$ alkoxyalkyl" and "$C_{1-6}$ haloalkyl" means the aforementioned $C_{1-6}$ alkyl groups substituted with an alkoxy group or one or more halogen atoms, such as methoxyethyl, ethoxyethyl, ethoxybutyl, dibromomethyl, trifluoromethyl, 1-chloroethyl, 1,1-dichloroethyl, 1-iodobutyl or pentafluoroethyl.

The term "$C_{2-6}$ alkynyl" is used herein to indicate an alicyclic hydrocarbon group having from 2 to 6 carbon atoms which contain a $-C\equiv C-$ group. However, it should be noted that the $-C\equiv C-$ group cannot be directly adjacent the nitrogen atom of the acylamino group.

"$C_{3-10}$ cycloalkyl" means a saturated ring having from 3 to 10 carbon atoms in the ring such as cyclopropyl, cyclobutyl, cyclopentyl, cyclooctyl, or adamantyl. "$C_{3-10}$ cycloalkyl-$C_{1-6}$ alkyl" means the aforementioned saturated rings attached to a $C_{1-6}$ alkylene bridge.

The term "optionally substituted phenyl" as used herein means a phenyl group unsubstituted or substituted by one or more groups which do not substantially alter the pharmacological activity of the compounds of formula (I), such as halogen, trifluoromethyl, methyl, methoxy, or nitro groups.

The term "$C_{2-6}$ carboxyalkyl" as used herein means a $C_{1-5}$ alkyl group substituted by a carboxylic acid group. Examples of such groups are carboxymethyl, carboxyethyl, carboxypropyl and carboxybutyl.

Compounds of formula (I) may be represented by the structural formulae:

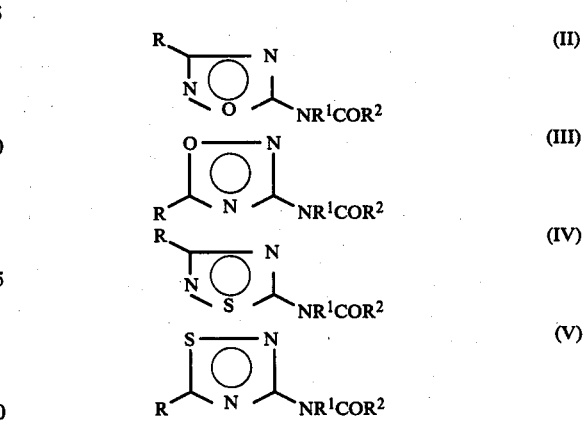

where $R^1$ and $R^2$ are as previously defined and R is hydrogen or the optional substituent on the heteroaryl nucleus.

Particularly interesting compounds of formula (I) to (V) are those wherein the heteroaryl group is substituted by a $C_{1-4}$ alkyl group, especially methyl, $R^1$ is $C_{1-6}$ alkyl, especially $C_{4-6}$ alkyl, $C_{3-5}$ alkenyl or benzyl and $R^2$ is $C_{3-6}$ alkyl, $C_{3-6}$ cycloalkyl or benzyl.

The compounds of formula (I) to (V) may be prepared by (a) acylating an alkyl derivative of formula:

$$ArNHR^1 \quad (VIII)$$

where Ar and $R^1$ are as defined previously; or
(b) alkylating an acyl derivative of formula:

ArNHCOR²             (IX)

where Ar and R² are as defined previously.

The acylation of the compound of formula (VIII) may be carried out with an acid halide having the formula R²CO—X wherein X is chlorine or bromine and R² is defined above in the presence of a proton acceptor, such as pyridine or triethylamine, in an inert solvent, such as benzene. The acylation may also be carried out by heating the alkyl derivative with a suitable acid anhydride, (R²CO)₂O, in an inert solvent.

Those skilled in the art will immediately appreciate that a wide variety of other acylating conditions can be used (see, for example, "The Chemistry of Amides" 1971 by A. J. Deckwith; "Survey of Organic Synthesis", 1970 by Buehler and Pearson; "Organic Functional Group Preparations" 1968 by Sandler and Karo; "Reagents for Organic Synthesis" 1968 by Fieser and Fieser, etc.).

Compounds of formula (IX) can be alkylated by dissolving the amide in a suitable inert, anhydrous, polar solvent such as dimethylformamide, forming an alkali metal salt thereof with an alkali metal hydride, preferably sodium hydride, and then treating the salt with an alkylating agent of formula R¹X¹ where X¹ is a reactive atom such as a halogen atom or a reactive group such as an alkyl sulphate group.

Alkylating agents and alkylating reaction conditions other than those specified above can be utilised, the nature of these being readily apparent to those acquainted with the art.

The derivatives of formulae (VIII) and (IX) can be derived from the corresponding amines of formula ArNH₂ by standard alkylation or acylation techniques.

The amines of formula ArNH₂ are either known compounds or can be prepared by modification of known synthetic methods.

The intermediates of formula (IX) except when (a) Ar is 1,2,4-thiadiazolyl unsubstituted or substituted by C₁₋₄alkyl, C₃₋₁₀cycloalkyl or optionally substituted phenyl and R² is C₁₋₄ alkyl or C₁₋₄ haloalkyl; and (b) Ar is 1,2,4-oxadiazolyl substituted by phenyl and R² is C₁₋₈ alkyl, are novel and are provided in a further aspect of the invention.

According to one aspect of the present invention there is provided a pharmaceutical formulation comprising a heteroaryl derivative of formula:

            (XIII)

wherein Ar represents a 5-membered heteroaryl nucleus selected from 1,2,4-thiadiazole and 1,2,4-oxadiazole, said heteroaryl nucleus being optionally substituted by formyl, carboxyl, hydroxyl, C₁₋₄hydroxyalkyl, C₁₋₄haloalkyl, C₁₋₄alkyl, C₃₋₁₀cycloalkyl, C₃₋₆acyloxyalkyl, optionally substituted phenyl or halogen, the acylamino group —NR¹COR² being attached to a carbon atom of the heteroaryl nucleus, and wherein R¹ is C₁₋₁₀ alkyl, C₂₋₆ alkenyl, C₃₋₆ alkynyl, C₂₋₆ alkoxyalkyl, C₂₋₆ carboxyalkyl, C₁₋₆ haloalkyl, C₃₋₁₀ cycloalkyl, C₃₋₁₀ cycloalkyl-C₁₋₆ alkyl, optionally substituted phenyl-C₁₋₆ alkyl or optionally substituted phenyl-C₂₋₆ alkenyl; and R² is C₁₋₈ alkyl, C₁₋₆ haloalkyl, C₂₋₆ alkenyl, C₃₋₁₀ cycloalkyl, C₃₋₁₀ cycloalkyl-C₁₋₆ alkyl, optionally substituted phenyl, optionally substituted phenyl-C₁₋₆ alkyl or optionally substituted phenyl-C₂₋₆ alkenyl; or R¹ and R² together form a lactam ring having 5 to 7 ring atoms; associated with a pharmaceutically acceptable carrier therefor.

Preferred pharmaceutical formulations comprise compounds of formula (I).

Compunds of formulae (I) and (XIII) have been shown to be useful in the prophylactic and therapeutic treatment of immediate hypersensitivity diseases including asthma and in the alleviation of status asthmaticus. The compounds have low toxicity.

The compounds or formulations of the present invention may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formulae (I) or (XIII). Dosages of from 0.5 to 300 mg/kg per day, preferably 0.5 to 20 mg/kg of active ingredient may be administered although it will, of course, readily be understood that the amount of the compound or compounds of formulae (I) or (XIII) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formulae (I) or (XIII) mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance.

Some examples of the diluents or carriers which may be employed in the pharmaceutical compositions of the present invention are lcatose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of thoobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichloroetetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

Preferred pharmaceutical forms of the present invention are capsules, tablets, suppositories, aerosols, injectible solutions, cremes and ointments.

The following Examples will further illustrate the invention.

EXAMPLE 1

(a) 5-Chloro-3-methyl-1,2,4-thiadiazole

A suspension of acetamidine hydrochloride (47.0 g, 0.50 mol) and trichloromethanesulfenyl chloride (83.0 g, 0.45 mol) in 500 ml dichloromethane was placed in a three-necked flask fitted with a stirrer, dropping funnel and thermometer. Cooling in an acetone bath and stirring, a solution of sodium hydroxide (100 g, 2.50 mol) in 150 ml water was added slowly, keeping the temperature below −8° C. by means of a cold plate. After about half of the solution had been added, upon further addition the colour changed from red through orange to yellow. After final addition (about five hours) the precipitated NaCl was filtered off and washed with $CH_2Cl_2$. The organic phase was separated from water, the latter being shaken 3 times with $CH_2Cl_2$ (30 ml). The combined $CH_2Cl_2$ solutions were washed with water until it became neutral and then dried over magnesium sulphate. The solvent was evaporated off to yield a red liquid. The liquid was distilled under vacuum to give 5-chloro3-methyl-1,2,4-thiadiazole as a colourless liquid. Yield 27 g (45%), b.p. 25° C./3.5 mm Hg.

(b) 5-Butylamino-3-methyl-1,2,4-thiadiazole

5-Chloro-3-methyl-1,2,4-thiadiazole (27 g, 0.20 mol) was dissolved in 200 ml ethanol and, under cooling in an ice bath, added to an ethanolic solution of butylamine (44 g, 0.60 mol), stirred at room temperature overnight and evaporated to small bulk. Upon addition of ether a white precipitate of butylamine hydrochloride formed which was filtered off. The yellow filtrate was washed with water, dried over magnesium sulphate, filtered and evaporated to dryness to yield a yellow oil which was distilled under vacuum to give 5-butylamino-3-methyl-1,2,4-thiadiazole as a pale yellow liquid. Yield 29.9 g, (87.2%), b.p. 101°-102° C./0.14 mmHg.

(c) N-(3-Methyl-1,2,4-thiadiazole-5-yl)-N-methylcyclohexane carboxamide

Cyclohexane carboxylic acid chloride (9.92 g, 0.068 mol) was added slowly to a solution of 5-methylamino-3-methyl-1,2,4-thiadiazole (7.0 g, 0.054 mol) in dry benzene containing triethylamine (6.87 g, 0.068 mol) and the mixture heated under reflux for 1½ hours, cooled and washed with 2 N hydrochloric acid, saturated solution sodium hydrogen carbonate and water; dried over magnesium sulphate, filtered and evaporated down to yield yellow oil which crystallised upon standing. This was recrystallised twice from petroleum ether 60°-80° C. to yield off-white crystals of N-(3-methyl-1,2,4-thiadiazol-5-yl)-N-methylcyclohexane carboxamide. Yield 8.23 g, (63.8%), m.p. 96° C.

EXAMPLES 2 TO 11

The following compounds were prepared by similar methods to that described in Example 1.

N-(3-Methyl-1,2,4-thiadiazol-5-yl)-N-butyl-2-methylpropanamide (b.p. 115°-117° C./0.1 mmHg).

Analysis: $C_{11}H_{19}N_3OS$ requires: C, 54.74; H, 7.93; N, 17.41; O, 6.63; S, 13.28%; found: C, 54.64; H, 7.97; N, 17.37; O, 6.48; S, 13.36%.

N-(3-Methyl-1,2,4-thiadiazol-5-yl)-N-butylcyclopropane carboxamide. (m.p. 43° C.).

N-Butyl-N-(3-methyl-1,2,4-thiadiazol-5-yl)benzamide (m.p. 77° C.)

N-(3-Cyclobutyl-1,2,4-thiadiazol-5-yl)-N-octylcyclooctane carboxamide.

N-Methyl-N-(3-methyl-1,2,4-thiadiazol-5-yl)benzeneacetamide (m.p. 86° C.).

N-(3-Methyl-1,2,4-thiadiazol-5-yl)-N-2-propenyl acetamide (m.p. 61° C.).

N-(3-Methyl-1,2,4-thiadiazol-5-yl)-N-methyl-2-methylpropanamide. (m.p. 54° C.).

N-(3-Methyl-1,2,4-thiadiazol-5-yl)-N-n-butyl-n-hexanamide (b.p. 130°-135° C./0.15 mmHg, purified by column chromatography).

Analysis: $C_{14}H_{25}N_3OS$ requires: C, 59.33; H, 8.89; N, 14.83; O, 5.65; S, 11.31%; found: C, 59.39; H, 8.82; N, 15.19; O, 5.87%.

N-(3-Methyl-1,2,4-thiadiazol-5-yl)-N-(2-propenyl)-benzeneacetamide (m.p. 70° C.).

N-(3-Methyl-1,2,4-thiadiazol-5-yl)-N-2-propenylcyclopropane carboxamide. (m.p. 76° C.).

EXAMPLE 12

3-Phenyl-5-trichloromethyl-1,2,4-oxadiazole

Trichloroacetic anhydride (154.4 g, 0.5 mole) was added to a stirred solution of benzamidoxime (34.0 g, 0.25 mole) in dry trichloroacetic acid (160 g) in an oil bath at ∼60° C. The reaction mixture was heated at 120° C. for 20 minutes and on cooling was poured into ice/water (400 ml). The organic layer was separated, washed with water and taken up in carbon tetrachloride (500 ml) and neutralised by washing with a saturated solution of $NaHCO_3$. After drying over $MgSO_4$ and evaporating off the carbon tetrachloride, the product was distilled. (b.p. 118° C./0.07 mmHg).

EXAMPLE 13

3-Methyl-5-trichloromethyl-1,2,4-oxadiazole was similarly prepared.

EXAMPLE 14

5-Butylamino-3-methyl-1,2,4-oxadiazole

3-Methyl-5-trichloromethyl-1,2,4oxadiazole (43 g, 0.21 mole) was added to n-butylamine (46.75 g, 0.63 mole) and stirred at room temperature overnight. Excess amine was removed under vacuum and the residue distilled (oil bath 110° C./0.5 mmHg). Recrystallisation from petroleum ether 60°-80° C. gave the title compound as white plates 26 g, m.p. 62°-65° C.

EXAMPLE 15

N-n-Butyl-N-(3-methyl-1,2,4-oxadiazol-5-yl)-n-butanamide

5-Butylamino-3-methyl-1,2,4-oxadiazole (4.2 g, 0.03 mole) and butyric anhydride (4.75 g, 0.033 mole) were refluxed in toluene (30 ml9 for 3 hours. After removing the toluene under vacuum, the residue was refluxed in methanol (60 ml) with a few drops of triethylamine for 1 hour. The methanol was evaporated under vacuum and residue taken up in $CH_2Cl_2$, washed twice with 2 N HCl and twice with a saturated solution of $NAHCO_3$ and dried over $MgSO_4$. The product was purified by column chromatography (silica gel 120 g) eluted with petroleum ether 40°–60° C., increasing solvent polarity to 10% ether/petroleum ether. Fractions were combined and distilled in a Kugelrohr airbath at 119° C./3.3 mmHg.

Analysis: $C_{11}H_{19}N_3O_2$ requires: C, 58.64; H, 8.50; N, 18.65; O, 14.20%; found: C, 58.78; H, 8.30; N, 18.40; O, 14.18%.

EXAMPLES 16–22

The following oxadizoles were prepared using the method described in Example 15.

N-Ethyl-N-(3-methyl-1,2,4-oxadiazol-5-yl)-2-methylpropanamide (b.p. 92° C./3.0 mmHg).

Analysis: $C_9H_{15}N_3O_2$ requires: C, 54.80; H, 7.66; N, 21.30; O, 16.22%; found: C, 54.68; H, 7.46; N, 21.14; O, 16.33%.

N-n-Butyl-N-(3-methyl-1,2,4-oxadiazol-5-yl)acetamide $\eta_{20}$ 1.4748, of liquid.

N-Butyl-N-(3-methyl-1,2,4-oxadiazol-5-yl)-2-methylpropanamide (b.p. (airbath temperature) 98° C./1.5 mmHg).

Analysis: $C_{11}H_{19}N_3O_2$ requires: C, 58.65; H, 8.50; N, 18.66; O, 14.20%; found: C, 58.49; H, 8.22; N, 18.40; O, 14.18%.

N-n-Butyl-N-(3-methyl-1,2,4-oxadiazol-5-yl)hexanamide

Analysis: $C_{13}H_{23}N_3O_2$ requires: C, 61.63; H, 9.15; N, 16.58; O, 12.63%; found: C, 61.89; H, 9.39; N, 16.33; O, 12.65%.

N-Ethyl-N-(3-Phenyl-1,2,4-oxadiazol-5-yl)-2-methylpropanamide (m.p. 48° C.).

N-Butyl-N-(3-phenyl-1,2,4-oxadiazol-5-yl)-2-methylpropanamide (b.p. 140° C./7 mmHg airbath temperature).

Analysis: $C_{16}H_{21}N_3O_2$ requires: C, 66.88; H, 7.37; N, 14.62; O, 11.14%; found: C, 67.07; H, 7.38; N, 14.38; O, 11.06%.

N-Ethyl-N-(3-phenyl-1,2,4-oxadiazol-5-yl)-n-butanamide (m.p. 74° C.).

EXAMPLE 23

N-n-Hexyl-N-(3-methyl-1,2,4-oxadiazol-5-yl)acetamide 5-n-Hexylamino-3-methyl-1,2,4-oxadiazole (4.6 g, 0.025 mole) was dissolved in acetic anhydride (25 ml) and refluxed for 3 hours and then evaporated down to dryness under vacuum. The residue was taken up in $CHCl_3$ (50 ml) and washed twice with 2 N HCl and twice with a saturated solution of $NaHCO_3$ and dried over $MgSO_4$. (b.p. 113°–114° C./1.0 mmHg).

Analysis: $C_{11}H_{19}N_3O_2$ requires: C, 58.64; H, 8.50; N, 18.65; O, 14.20%; found: C, 58.66; H, 8.76; N, 18.57; O, 14.48%.

EXAMPLE 24

The following oxadiazole was similarly prepared using the process of Example 23.

N-(3-Methyl-1,2,4-oxadiazol-5-yl)-N-2-propenylacetamide (b.p. 82° C./1.5 mmHg airbath temperature).

Analysis: $C_8H_{11}N_3O_2$ requires: C, 53.02; H, 6.12; N, 23.19; O, 17.66%; found: C, 52.78; H, 5.90; N, 23.03; O, 17.69%.

EXAMPLE 25

N-(3-methyl-1,2,4-oxadiazol-5-yl)-N-[(4-methylphenyl)methyl]cyclopropanecarboxamide Cyclopropane carboxylic acid chloride (3.45 g, 0.033 mole) was added dropwise to a solution of 5-(4-methylphenyl)methylamino-3-methyl-1,2,4-oxadiazole (6.1 g, 0.03 mole) and triethylamine (3.45 g, 0.035 mole) in dry benzene keeping the temperature below 10° C. After the addition the temperature was allowed to reach room temperature and then refluxed overnight. On cooling the reaction mixture was washed twice with 2 N HCl and twice with a saturated solution of $NaHCO_3$ and dried over $MgSO_4$ and charcoaled. The product was purified by column chromatography—silica gel (110 g) eluting with petroleum ether 40°–60° C. increasing polarity to 10% ether in petroleum ether. The title compound was recrystallised from petroleum ether 60°–80° C. as white needles. m.p. 49.5°–50.5° C.

EXAMPLES 26–37

The following further oxadiazoles were prepared using the process of Example 25.

N-Methyl-N-(3-methyl-1,2,4-oxadiazol-5-yl)benzamide (m.p. 74° C.).

N-n-Butyl-N-(3-methyl-1,2,4-oxadiazol-5-yl)cyclopropane carboxamide ($\eta_D^{26}$ 1.4882).

N-Hexyl-N-(3-methyl-1,2,4-oxadiazol-5-yl)cyclopentane carboxamide (b.p. 121° C./1.4 mmHg (airbath temperature).

Analysis: $C_{15}H_{25}N_3O_2$ requires: C, 64.48; H, 9.02; N, 15.04; O, 11.52%; found: C, 64.76; H, 8.86; N, 14.82; O, 11.52%.

N-Hexyl-N-(3-methyl-1,2,4-oxadiazol-5-yl)cyclohexane carboxamide (b.p. 157° C./1.5 mmHg airbath temperature).

Analysis: $C_{16}H_{27}N_3O_2$ requires: C, 65.49; H, 9.27; N, 14.32; O, 10.9%; found: C, 65.68; H, 9.05; N, 14.19; O, 10.95%.

N-Hexyl-N-(3-methyl-1,2,4-oxadiazol-5-yl)benzamide (b.p. 126° C./0.2 mmHg airbath temperature).

Analysis: $C_{16}H_{21}N_3O_2$ requires: C, 66.87; H, 7.36; N, 14.62; O, 11.13%; found: C, 66.85; H, 7.35; N, 14.58; O, 11.27%.

N-(3-Methyl-1,2,4-oxadiazol-5-yl)-N-2-propenylcyclopropane carboxamide (b.p. 120° C./10 mmHg airbath temperature).

N-(3-Methyl-1,2,4-oxadiazol-5-yl)-N-(phenylmethyl)cyclohexanecarboxamide (m.p. 73° C.).

N-(3-Methyl-1,2,4-oxadiazol-5-yl)-N-(phenylmethyl)benzamide (m.p. 75° C.).

N-(3-Methyl-1,2,4-oxadiazol-5-yl)-N-phenylmethyl-2-methylpropanamide (b.p. 127° C./3.00 mmHg).

N-(4-Methoxyphenyl)methyl-N-(3-methyl-1,2,4-oxadiazol-5-yl)cyclohexane carboxamide (m.p. 70° C.).

N-(4-Methoxyphenyl)methyl-N-(3-methyl-1,2,4-oxadiazol-5-yl)-2-methylpropanamide (b.p. 118° C. at 0.2 mmHg airbath temperature).

N-(4-Methylphenyl)methyl-N-(3-methyl-1,2,4-oxadiazol-5-yl)cyclopropane carboxamide (m.p. 50° C.).

EXAMPLE 38

N-(1-Methylethyl)-N-(3-methyl-1,2,4-oxadiazol-5-yl)-2-methylpropanamide isoButyric anhydride (7.9 g, 0.05 mole) was added to isopropylamino-3-methyl-1,2,4-oxadiazole and heated at 100° C. overnight. On cooling, methanol (60 ml) and a few drops of triethylamine was added and refluxed for 1 hour. After removal of the methanol under vacuum, the residue was taken up in ether and washed twice with a saturated solution of NaHCO$_3$. (b.p. 90° C./1.3 mmHg Kugelrohr airbath temperature).

EXAMPLE 39

The following 1,2,4-oxadiazole was prepared using a similar method to that described in Example 15.

N-n-Hexyl-N-(3-methyl-1,2,4-oxadiazol-5-yl)-2-methyl propanamide (b.p. 90° C./1.1 mmHg).

Analysis: $C_{13}H_{23}N_3O_2$ requires: C, 61.63; H, 9.15; N, 16.58; O, 12.63%; found: C, 61.47; H, 8.98; N, 16.84; O, 12.70%.

EXAMPLES 40-42

Similarly, using the process generally described in Example 25, the following further oxadiazoles were prepared:

N-methyl-N-(3-methyl-1,2,4-oxadiazol-5-yl)-cyclohexane carboxamide

Analysis: $C_{11}H_{17}N_3O_2$ requires: C, 59.17; H, 7.67; N, 18.82; O, 14.33%; found: C, 59.05; H, 7.59; N, 18.41; O, 14.73%.

N-(3-methyl-1,2,4-oxadiazol-5-yl)-N-2 propenyl heptanamide (b.p. 104° C./1.5 mmHg).

Analysis: $C_{13}H_{21}N_3O_2$ requires: C, 62.12; H, 8.42; N, 16.71; O, 12.73%; found: C, 62.16; H, 8.20; N, 16.54; O, 12.63%.

N-(3-methyl-1,2,4-oxadiazol-5-yl)-N-n-butyl-2-ethyl butanamide (b.p. 71° C./0.055 mmHg).

Analysis: $C_{13}H_{23}N_3O_2$ requires: C, 61.63; H, 9.15; N, 16.59; O, 12.63%; found: C, 61.46; H, 8.90; N, 16.57; O, 12.47%.

EXAMPLE 43

N-(3-methyl-1,2,4-thiadiazol-5-yl)N-phenylmethyl-n-hexanamide (m.p. 72° C.) was prepared using the procedure outlined in Example 1.

EXAMPLES 44 TO 46

The following further 1,2,4-thiadiazoles were prepared by similar methods to that used in Example 1.

N-(3-Methyl-1,2,4-thiadiazol-5-yl)-N-hexyl acetamide (m.p. 38° C.).

N-Hexyl-N-(3-methyl-1,2,4-thiadiazol-5-yl)benzeneacetamide (m.p. 57° C.).

N-(3-Methyl-1,2,4-thiadiazol-5-yl)-N-(phenylmethyl)benzeneacetamide

EXAMPLES 47 TO 55

The following further 1,2,4-oxadiazoles were prepared by similar methods to that used in Example 25.

N-Butyl-N-(3-methyl-1,2,4-oxadiazol-5-yl)-phenyl carboxamide.

Analysis: $C_{14}H_{12}N_3O_2$ requires: C, 64.84; H, 6.61; N, 16.21; O, 12.34; found: C, 65.09; H, 6.35; N, 15.99; O, 12.07.

N-Butyl-N-(3-methyl-1,2,4-oxadiazol-5-yl)-4-chlorophenyl carboxamide.

Analysis: $C_{14}H_{16}ClN_3O_2$ requires: C, 57.24; H, 5.49; Cl, 12.07; N, 14.30; O, 10.89; found: C, 57.45; H, 5.63; Cl, 12.07; N, 14.14 O, 11.17.

N-Butyl-N-(3-methyl-1,2,4-oxadiazol-5-yl)-4-methoxyphenyl carboxamide. (b.p. 105° C./0.015 mmHg).

Analysis: $C_{15}H_{19}N_3O_3$ requires: C, 62.27; H, 6.62; N, 14.52; O, 16.59; found: C, 61.99; H, 6.47; N, 14.42; O, 16.74.

N-Butyl-N-(3-methyl-1,2,4-oxadiazol-5-yl)-cyclohexane carboxamide. (b.p. 70° C./0.01 mmHg).

Analysis: $C_{14}H_{23}N_3O_2$ requires: C, 63.37; H, 8.74; N, 15.84; found: C, 63.54; H, 8.55; N, 15.60.

N-Butyl-N-(3-methyl-1,2,4-oxadiazol-5-yl)-cyclobutane carboxamide. (b.p. 67° C./0.02 mmHg).

Analysis: $C_{12}H_{19}N_3O_2$ requires: C, 60.74; H, 8.07; N, 17.71; O, 13.49; found: C, 60.44; H, 7.88; N, 17.54; O, 13.21.

N-(3-Methyl-1,2,4-oxadiazol-5-yl)-N-propyl 2-methyl propanamide. (b.p. 62° C./0.15 mmHg).

Analysis: $C_{10}H_{17}N_3O_2$ requires: C, 56.85; H, 8.11; N, 19.89; found: C, 56.93; H, 8.14; N, 19.64.

N-Butyl-N-(3-butyl-1,2,4-oxadiazol-5-yl)-cyclopropane carboxamide.

Analysis: $C_{14}H_{23}N_3O_2$ requires: C, 63.37; H, 8.74; N, 15.84; O, 12.06; found: C, 63.19; H, 8.51; N, 15.58; O, 11.82.

N-Butyl-N-(3-ethyl-1,2,4-oxadiazol-5-yl)-cyclopropane carboxamide. (b.p. 65° C./0.01 mmHg).

Analysis: $C_{12}H_{19}N_3O_2$ requires: C, 60.74; H, 8.07; N, 17.71; O, 13.49; found: C, 60.50; H, 7.78; N, 17.43; O, 13.19.

N-Butyl-N-(3-cyclohexyl-1,2,4-oxadiazol-5-yl)-cyclopropane carboxamide.

Analysis: $C_{16}H_{25}N_3O_2$ requires: C, 65.95; H, 8.65; N, 14.42; O, 10.98; found: C, 66.15; H, 8.83; N, 14.51; O, 10.86.

EXAMPLES 56 TO 58

Similarly, by methods similar to that used in Example 38, the following further oxadiazoles were prepared:

N-Butyl-N-(3-ethyl-1,2,4-oxadiazol-5-yl)-2-methyl-propanamide. (b.p. 65° C./0.02 mmHg).

Analysis: $C_{12}H_{21}N_3O_2$ requires: C, 60.22; H, 8.85; N, 17.56; O, 13.37; found: C, 59.96; H, 8.68; N, 17.36; O, 13.22.

N-Butyl-N-(3-butyl-1,2,4-oxadiazol-5-yl)-2-methyl propanamide. (b.p. 64° C./0.05 mmHg).

Analysis: $C_{14}H_{25}N_3O_2$ requires: C, 62.89; H, 9.42; N, 15.72; O, 11.97; found: C, 62.65; H, 9.20; N, 15.46; O, 11.72.

N-Butyl-N-(3-cyclohexyl-1,2,4-oxadiazol-5-yl)-2-methylpropanamide. (b.p. 92° C./0.02 mmHg).

Analysis: $C_{16}H_{27}N_3O_2$ requires: C, 65.49; H, 9.28; N, 14.32; O, 10.91; found: C, 65.26; H, 9.09; N, 14.07; O, 11.05.

The following Examples 59 to 66 illustrate pharmaceutical formulations containing the active compound N-n-hexyl-N-(3-methyl-1,2,4-oxadiazol-5-yl)-cyclopentane carboxamide.

EXAMPLE 59

Soft gelatin capsules were prepared using the following ingredients:

|  | Quantity (mg/capsule) |
| --- | --- |
| Active compound | 30 |
| Butylated hydroxyanisole B.P. | 0.02 |
| Fractionated Coconut Oil B.P.C. | 70 |
|  | 100.02 |

The above ingredients were mixed and filled into soft gelatin capsules, the main shell components of which were gelatin and glycerine.

EXAMPLE 60

The procedure of Example 60 was repeated except that an identical quantity of propyl gallate was used in place of the butylated hydroxyanisole as antioxidant.

EXAMPLE 61

Hard gelatin capsules were prepared using the following ingredients:

|  | Quantity (mg/capsule) |
| --- | --- |
| Active compound | 23 |
| Silicon dioxide (fumed) | 23 |
| Lactose | 48 |
| Butylated hydroxyanisole B.P. | 0.02 |

The butylated hydroxyanisole was dissolved in the active ingredient and the solution so formed adsorbed onto the silicon dioxide (fumed). The lactose was then added and the whole mixed. Finally, the mixture was filled into hard gelatin capsules.

EXAMPLE 62

An ointment was made up from the following ingredients:

| Active compound | 1.5% by weight |
| --- | --- |
| Butylated hydroxyanisole B.P. | 0.02% by weight |
| White soft paraffin | q.s. 100% |

The hydroxyanisole was dissolved in the melted paraffin and the active compound then added in, and the mixture allowed to cool.

EXAMPLE 63

A topical cream containing 1.0% of the compound is prepared as follows:

|  | grams |
| --- | --- |
| Active compound | 1.0 |
| Cetomacrogol 1000 | 3.0 |
| Cetostearyl alcohol | 11.5 |
| Liquid Paraffin | 9.0 |
| Butylated hydroxyanisole B.P. | 0.02 |
| Distilled water | to 100.0 |

The compound was mixed with the hydroxyanisole and suspended in the liquid paraffin. The cetostearyl alcohol was added and the mixture heated to 70° C. with stirring. The cetomacrogol 1000 was dissolved in 60 g. of water heated to 70° C. The cetostearyl alcohol and liquid paraffin active compound mixture were then poured into the aqueous cetomacrogol 1000 solution with stirring and the stirring continued until the cream was cold. The cream was then made up to weight with water and passed through a stainless steel colloid mill set at a gap of 15/1000 inch.

EXAMPLE 64

Suppositories containing 25 and 50 mg. of the compound were prepared as follows:

| Active compound | 2.5 g. |
| --- | --- |
| Henkel base | 97.5 g. |

The active compound was mixed with the Henkel base which had been previously melted using the minimum amount of heat possible. The mixture was then poured into suppository moulds of a nominal capacity of 1 g. or 2 g. as desired, to produce suppositories each containing 25 mg. or 50 mg. of the active compound.

EXAMPLE 65

An aerosol was prepared containing the following ingredients:

|  | Quantity per ml. |
| --- | --- |
| Active compound | 10.00 mg. |
| Propylene glycol | 10.00 mg. |
| Dichlorotetrafluoroethane (Propellant 114) | 550.00 mg. |
| Dichlorodifluoromethane (Propellant 12) | 830.00 mg. |

The active compound was mixed with the propylene glycol and the mix added to the propellant 114, the mixture cooled to $-15°$ to $-20°$ C. and transferred to a filling device. At the same time a mixture of propellants 114 and 12, previously cooled to $-15°$ to $-20°$ C. was fed into a second filling device. A metered amount of propellant from the second filling device was introduced into a stainless steel container, followed by the required amount of material from the first filling device. The valve units were then fitted and sealed to the container. These valve units were equipped with a metering device so that approximately 0.15 mg. of the active compound is released by a single actuation of the valve.

EXAMPLE 66

Tablets were prepared using the following components:

| Active compound | 10.00 mg. |
| --- | --- |
| Microcrystalline Cellulose | 250.00 mg. |
| Sodium Carboxymethyl Starch | 25.00 mg. |
| Magnesium Stearate | 3.00 mg. |
| Butylated Hydroxyanisole B.P. | 0.002 mg. |

The hydroxyanisole was dissolved in the active compound, the solution adsorbed onto the microcrystalline cellulose. This was mixed with the sodium carboxymethyl starch and then the magnesium stearate was mixed in. Finally, the mixture was compressed to form tablets.

In the foregoing Examples 59 to 66, the liquid active compound used may, in accordance with the invention, be replaced wholly or in part by other liquid active compounds of formula (I) or (XIII). If the active compound is a solid, appropriate modification will of course have to be made.

We claim:

1. A compound selected from the group consisting of:

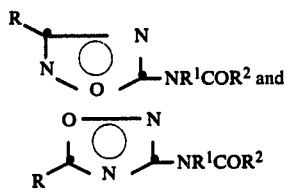

wherein R is $C_{1-4}$ hydroxyalkyl, $C_{1-4}$ alkyl, $C_{3-10}$ cycloalkyl, or optionally $R^3$-substituted phenyl and wherein $R^1$ is $C_{1-10}$ alkyl, $C_{2-6}$ alkenyl, $C_{2-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, optionally $R^3$-substituted phenyl-$C_{1-6}$ alkyl, or optionally $R^3$-substituted phenyl-$C_{2-6}$ alkenyl; $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, optionally $R^3$-substituted phenyl, optionally $R^3$-substituted phenyl-$C_{1-6}$ alkyl, or optionally $R^3$-substituted phenyl-$C_{2-6}$ alkenyl; and $R^3$ is halogen, trifluoromethyl, $C_{1-3}$ alkyl, $C_{1-3}$ alkoxy or nitro; provided that: when R is phenyl and $R^2$ is methyl, $R^1$ cannot be methyl or benzyl; and when $R^1$ is $C_{2-6}$ alkynyl, the —C≡C— group cannot be directly adjacent to the nitrogen atom of the acylamino group.

2. A compound of claim 1 wherein R is $C_{1-4}$ alkyl, $C_{3-8}$ cycloalkyl or phenyl; $R^1$ is $C_{1-8}$ alkyl, $C_{3-6}$ alkenyl or benzyl optionally substituted by $C_{1-3}$ alkoxy or $C_{1-3}$ alkyl and $R^2$ is $C_{2-6}$ alkyl, $C_{3-8}$ cycloalkyl, benzyl or phenyl optionally substituted by halogen or $C_{1-3}$ alkoxy.

3. A compound according to claim 2, wherein R is $C_{1-4}$ alkyl; $R^1$ is $C_{1-6}$ alkyl, $C_{3-5}$ alkenyl or benzyl and $R^2$ is $C_{3-6}$ alkyl, $C_{3-6}$ cycloalkyl or benzyl.

4. A compound of claim 1 wherein $R^1$ is $C_{1-8}$ alkyl, $C_{3-6}$ alkenyl, $C_{3-8}$ cycloalkyl and benzyl optionally substituted by halogen, $C_{1-4}$ alkyl or $C_{1-4}$ alkoxy, and $R^2$ is $C_{1-8}$ alkyl, $C_{3-8}$ cycloalkyl, benzyl and phenyl optionally substituted by halogen or $C_{1-4}$ alkoxy.

5. The compound which is N-(3-methyl-1,2,4-thiadiazol-5-yl)-N-methylphenyl acetamide.

6. The compound which is N-(3-methyl-1,2,4-thiadiazol-5-yl)-N-2-propenylcyclopropane carboxamide.

7. A compund according to claim 2 being N-n-butyl-N-(3-methyl-1,2,4-oxadiazol-5-yl)-n-butanamide.

8. A compound according to claim 2 being N-ethyl-N-(3-methyl-1,2,4-oxadiazol-5-yl)-2-methylpropanamide.

9. A compound according to claim 2 being N-butyl-N-(3-methyl-1,2,4-oxadiazol-5-yl)-2-methylpropanamide.

10. A compound according to claim 2 being N-butyl-N-(3-methyl-1,2,4-oxadiazol-5-yl)-hexanamide.

11. A compound according to claim 2 being N-ethyl-N-(3-phenyl-1,2,4-oxadiazol-5-yl)-2-methylpropanamide.

12. A compound according to claim 2 being N-n-butyl-N-(3-methyl-1,2,4-oxadiazol-5-yl)-cyclopropane carboxamide.

13. A compound according to claim 2 being N-hexyl-N-(3-methyl-1,2,4-oxadiazol-5-yl)-cyclopentane carboxamide.

14. A compound according to claim 2 being N-(3-methyl-1,2,4-oxadiazol-5-yl)-N-2-propenylcyclopropane carboxamide.

15. A compound according to claim 2 being N-(3-methyl-1,2,4-oxadiazol-5-yl)-N-phenylmethyl-2-methylpropanamide.

16. A compound according to claim 2 being N-butyl-N-(3-methyl-1,2,4-oxadiazol-5-yl)-phenyl carboxamide.

17. A compound according to claim 2 being N-butyl-N-(3-methyl-1,2,4-oxadiazol-5-yl)-cyclohexane carboxamide.

18. A compound according to claim 2 being N-(3-methyl-1,2,4-oxadiazol-5-yl)-N-propyl-2-methylpropanamide.

19. A compound according to claim 2 being N-butyl-N-(3-ethyl-1,2,4-oxadiazol-5-yl)-cyclopropane carboxamide.

20. A compound according to claim 2 being N-butyl-N-(3-ethyl-1,2,4-oxadiazol-5-yl)-2-methylpropanamide.

21. A compound according to claim 2 being N-butyl-N-(3-cyclohexyl-1,2,4-oxadiazol-5-yl)-2-methylpropanamide.

* * * * *